(12) United States Patent
Pernodet et al.

(10) Patent No.: US 9,539,196 B2
(45) Date of Patent: Jan. 10, 2017

(54) COMPOSITIONS COMPRISING A SIRT6 ACTIVATOR AND A DNA REPAIR ENZYME

(71) Applicant: ELC Management LLC

(72) Inventors: Nadine Pernodet, Huntington Station, NY (US); Kelly Dong, Merrick, NY (US); Edward Pelle, Valley Stream, NY (US)

(73) Assignee: ELC MANAGEMENT, LLC, Melville, NY (US)

( * ) Notice: Subject to any disclaimer, the term of this patent is extended or adjusted under 35 U.S.C. 154(b) by 0 days.

(21) Appl. No.: 14/949,967

(22) Filed: Nov. 24, 2015

(65) Prior Publication Data

US 2016/0158139 A1    Jun. 9, 2016

Related U.S. Application Data

(60) Provisional application No. 62/089,618, filed on Dec. 9, 2014.

(51) Int. Cl.

| | | |
|---|---|---|
| *A61K 38/08* | (2006.01) | |
| *C07K 7/04* | (2006.01) | |
| *A61K 8/66* | (2006.01) | |
| *A61Q 17/04* | (2006.01) | |
| *A61K 8/64* | (2006.01) | |
| *A61Q 19/08* | (2006.01) | |

(52) U.S. Cl.
CPC . *A61K 8/66* (2013.01); *A61K 8/64* (2013.01); *A61Q 17/04* (2013.01); *A61Q 19/08* (2013.01); *C12Y 402/99018* (2013.01)

(58) Field of Classification Search
None
See application file for complete search history.

(56) References Cited

U.S. PATENT DOCUMENTS

| | | | |
|---|---|---|---|
| 8,569,243 B2 * | 10/2013 | Dal Farra | A61K 8/64 514/18.6 |
| 9,125,843 B2 * | 9/2015 | Pernodet | A61K 8/975 |
| 9,333,159 B2 * | 5/2016 | Hayes | A61K 8/27 |
| 2011/0318284 A1 | 12/2011 | Dal Farra et al. | |
| 2015/0098963 A1 | 4/2015 | Pernodet et al. | |

OTHER PUBLICATIONS

Revoris—Advanced Anti-Wrinkle Cream for Younger Skin Everyone Will Envy; http://revoris.com; accessed Dec. 3, 2014.

* cited by examiner

*Primary Examiner* — Satyanarayana R Gudibande
(74) *Attorney, Agent, or Firm* — Peter Giancana

(57) ABSTRACT

Compositions of the invention comprise 8-oxoguanine glycosylase (OGG1) and SIRT6 activating peptide G-A-G-V-S-A-E-$NH_2$. Compositions of the invention exhibit anti-aging effects by promoting the repair of skin cell DNA and/or by protecting skin cell DNA from UV damage.

2 Claims, 2 Drawing Sheets

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (7)..(7)
<223> OTHER INFORMATION: AMIDATION

<400> SEQUENCE: 1

Gly Ala Gly Val Ser Ala Glu
1               5
```

COMPOSITIONS COMPRISING A SIRT6 ACTIVATOR AND A DNA REPAIR ENZYME

FIELD OF THE INVENTION

The invention is in the field of treatments for improving the appearance of aging skin. More specifically, the invention pertains to topical compositions and methods that promote the protection and/or repair of DNA in skin cells damaged by ultraviolet light.

BACKGROUND OF THE INVENTION

Sirtuins are enzymes that play critical roles in many cellular epigenetic or metabolic pathways. In mammalian cells, seven sirtuin homologs have been identified, referred to as SIRTUINS 1-7 or SIRT1-7. SIRT6 is localized in the cell nucleus (of human keratinocytes and dermal fibroblasts, for example) and is a member of the conserved family of sirtuin proteins which are associated with metabolism and longevity. SIRT6 is a histone 3, lysine 9 (H3K9) deacetylase, and is primarily involved in DNA repair and telomere stability.

The term "SIRT6 activating peptide" means a peptide that causes the amount of SIRT6 in the cell to increase by whatever pathway causes that result. US2011-0318284, which is hereby incorporated by reference in its entirety, discloses compositions comprising SIRT6 activating peptides. The peptides are derived from highly conserved regions of human SIRT proteins. Of the eight peptide sequences disclosed in US2011-0318284, the following sequence is of interest here:

```
                                        (SEQ ID No. 1)
G-A-G-V-S-A-E-NH2
Gly-Ala-Gly-Val-Ser-Ala-Glu-NH2
```

Note that the $NH_2$ group on the C-terminal end of the peptide has been substituted onto the peptide to improve the resistance of the peptide to certain forms of degradation. $NH_2$ in that position does not occur naturally.

This peptide was reported to increase sirtuin 6 expression very significantly in normal human fibroblasts and normal human keratinocytes in short-term cultures. In addition, the sirtuin 6 expression stimulation effect was maintained for the long term. According to the reference, the activating peptides may be used alone or in combination with at least one other active agent, in a physiologically acceptable medium. The reference also discloses the utilization of a cosmetic composition to prevent and/or repair DNA degradation, improve telomere maintenance and reduce cellular senescence. However, US2011-0318284 makes no mention of *Arabidopsis thaliana*.

Co-pending application U.S. Ser. No. 14/045,075, filed Oct. 3, 2013 discloses compositions comprising the same SIRT6 activating peptides as US2011-0318284. According to this reference, a SIRT6 activating peptide may be present in the composition in amounts ranging from 0.0001 to 8%, preferably from about 0.001 to 3%, more preferably from about 0.01 to 1%. In a preferred embodiment, the activating peptide is supplied as a component of a yeast extract.

U.S. Ser. No. 14/045,075 also reports that a dose dependent increase in SIRT6 expression in Normal Human Epidermal Keratinocytes (NHEK) was caused by the SIRT6 activating peptide:

```
                                        (SEQ ID No. 1)
G-A-G-V-S-A-E-NH2
Gly-Ala-Gly-Val-Ser-Ala-Glu-NH2
```

It has been further reported that an unexpected increase in collagen synthesis in normal human dermal fibroblasts is caused by a combination of *Laminaria digitata* extract, *Narcissus tazetta* bulb extract, and a yeast protein extract that contains this SIRT6 activating peptide (SEQ ID 1). Furthermore, U.S. Ser. No. 14/045,075 mentions *Arabidopsis thaliana* extract in a long list of optional botanical extracts, wherein the suggested ranges for the one or more optional botanical extracts are reported as about 0.0001 to 10%, preferably about 0.0005 to 8%, more preferably about 0.001 to 5% by weight of the total composition. However, the *Arabidopsis thaliana* extract is not noted for any particular activity, and no synergy is disclosed between *Arabidopsis thaliana* extract and any of the SIRT6 activating peptides disclosed therein.

*Arabidopsis thaliana* Extract Containing 8-Oxoguanine Glycosylase

8-Oxoguanine glycosylase (OGG1) is a DNA repair enzyme that excises 8-oxoguanine, a base byproduct resulting from exposure to reactive oxygen species and ionizing radiation. OGG1 is active in both genomic and mitochondrial DNA, including in skin cells. 8-Oxoguanine glycosylase can be obtained by yeast fermentation of the plant *Arabidopsis thaliana*. *Arabidopsis thaliana* is a species in the Brassicaceae family, and is well known, as it is one of the model organisms used for studying plant biology. 8-Oxoguanine glycosylase extract from *Arabidopsis thaliana* ferment is commercially available in a liposomal formulation containing lecithin and water under the tradename Roxisomes™, from Barnet Products Corp., Englewood Cliffs, N.J. About 0.5% of the Roxisome™ is 8-Oxoguanine glycosylase.

Revoris is a commercially available wrinkle treatment product that reportedly comprises Roxisomes™ and two peptides: palmitoyl oligopeptide (a three amino acid peptide) and palmitoyl tetrapeptide-7 (a four amino acid peptide). Neither of these peptides is the same as nor suggests the 7 amino acid peptide SEQ. ID 1. No synergy is suggested between the Roxisomes and the peptides of Revoris.

SUMMARY

Compositions of the invention comprise 8-oxoguanine glycosylase (OGG1) and the following SIRT6 activating peptide.

```
                                        (SEQ ID No. 1)
G-A-G-V-S-A-E-NH2
Gly-Ala-Gly-Val-Ser-Ala-Glu-NH2
```

Compositions of the invention exhibit anti-aging effects by promoting the repair of skin cell DNA and/or by protecting skin cell DNA from ultraviolet damage.

DETAILED DESCRIPTION

All percentages mentioned herein are percentages by weight of the total composition, unless otherwise indicated.

Test Example 1

We have demonstrated that treatment of normal human epidermal keratinocytes (NHEK) by a SIRT6 activator (peptide SEQ ID No. 1) significantly reduced DNA fragmentation caused by UVB radiation. A description of the treatment follows.
Sample Preparation This study used control samples and three types of test samples. Control samples were neither treated with the peptide, nor exposed to UVB radiation. Type 1 samples were treated with the peptide, as described below, but not exposed to UVB radiation. Type 2 samples were not treated with the peptide, but were exposed to UVB radiation. Type 3 samples were treated with the peptide, as described below, and exposed to UVB radiation. SIRT6 activating peptide (SEQ ID No. 1) in powdered form was prepared in solution at 50 ppm.

For all test samples, Normal Human Epidermal Keratinocytes (NHEK) were seeded on Trevigen Flare™ slides at 8,000 cells/spot for DNA fragmentation analysis. Cells were incubated at 37° C., 95% humidity and 5% $CO_2$ in cell culture media for 24 hours. Type 1 and type 3 samples were treated with the 50 ppm powdered peptide solution at 3% of the cell culture media (equivalent to 0.00015% of peptide in solution), and all samples were incubated for 48 hours. Thereafter, the cell culture media was removed from all samples and replaced with 100 µl of Dulbecco's Phosphate Buffered Saline. Type 2 and type 3 samples were exposed to 20 mJ/cm$^2$ of UVB radiation, in an irradiation chamber from Opsytec Dr. Gröbel. Thereafter, the type 1 and type 3 samples were again treated with the powdered peptide solution at 3% of the cell media, and all samples were incubated for 6 hours, prior to comet assay.

Figure 1:
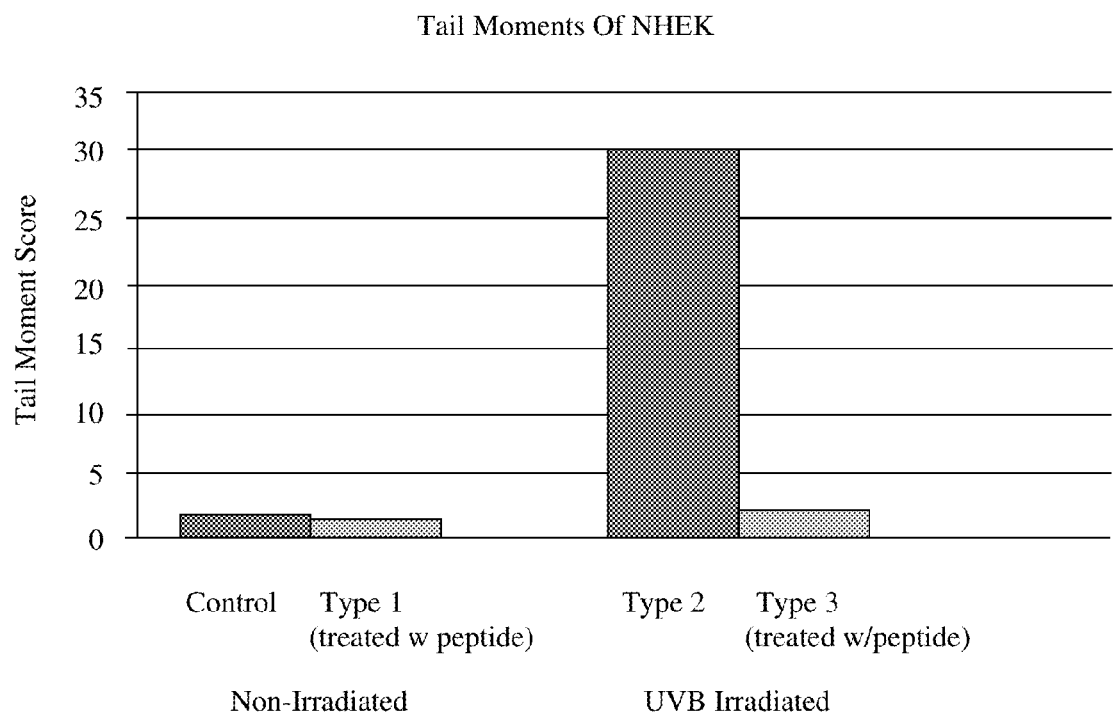
FIG. 1 shows the effects of SIRT6 activating peptide (SEQ ID No. 1) on DNA fragmentation in NHEK exposed to UVB radiation.

Following the six hour incubation, the sample cells were washed with phosphate buffered saline. 75 µl of melted agarose held at 37° C. was pipetted evenly on to each spot of the comet slide, and then incubated at 4° C. for 10 minutes. Slides were immersed in cold lysis solution on ice for 3 hours. Slides were removed from the lysis solution and placed into an alkaline solution (300 mM NaOH, 1 mM EDTA, pH>13) at room temperature for 30 minutes. At this point the cells are dead and cannot repair DNA any further. Subsequently, the slides were placed in an electrophoresis apparatus chilled in ice so that they were equidistant from the electrodes. Cold alkaline electrophoresis solution (300 mM NaOH, 1 mM EDTA, pH>13) was poured into the apparatus so that it just covered the slides. Electrophoresis ran for 30 minutes at 23V. After electrophoresis, the slides were rinsed in water, and immersed in 70% EtOH for 5 minutes. Slides were removed from the EtOH solution, and placed on a towel to air dry overnight. SYBR® Green 1 nucleic acid stain (Molecular Probes, Inc., Eugene Oreg.) was diluted in TE buffer (10 mM Tris-HCl, 1 mM EDTA, pH 7.5) to 1:10000. 50 µl of the diluted SYBR® Green 1 was pipetted on to each spot. SYBR® Green I binds to DNA and forms a complex that and emits green light at 520 nm. Slides were incubated at 4° C. for 5 minutes. After removing excess stain from the slides, the slides were allowed to dry again. Slides were viewed under an Olympus BX51 microscope with an FITC (fluorescein isothiocyanate) filter, with the 20× objective. Images were captured using the Nikon Elements software. The tail moments were analyzed with the Comet Score software from TriTek, Corp (Sumerduck, Va.). Results follow.
Results Referring to FIG. 1, type 1 samples (treated with SIRT6 activator peptide SEQ ID No. 1, but not irradiated) had DNA fragmentation comparable to the control samples. Type 2 samples (exposed to UVB radiation, but not treated with the peptide) showed about a fourteen fold increase in DNA damage. Type 3 samples (pre-treated with the peptide, exposed to UVB radiation, and post-treated treated with the peptide) had DNA fragmentation comparable to the control samples. We conclude that peptide SEQ ID No. 1 stimulates SIRT6 levels in NHEK leading to repair of DNA fragmentation caused by UVB radiation.

Test Example 2

Figure 2:
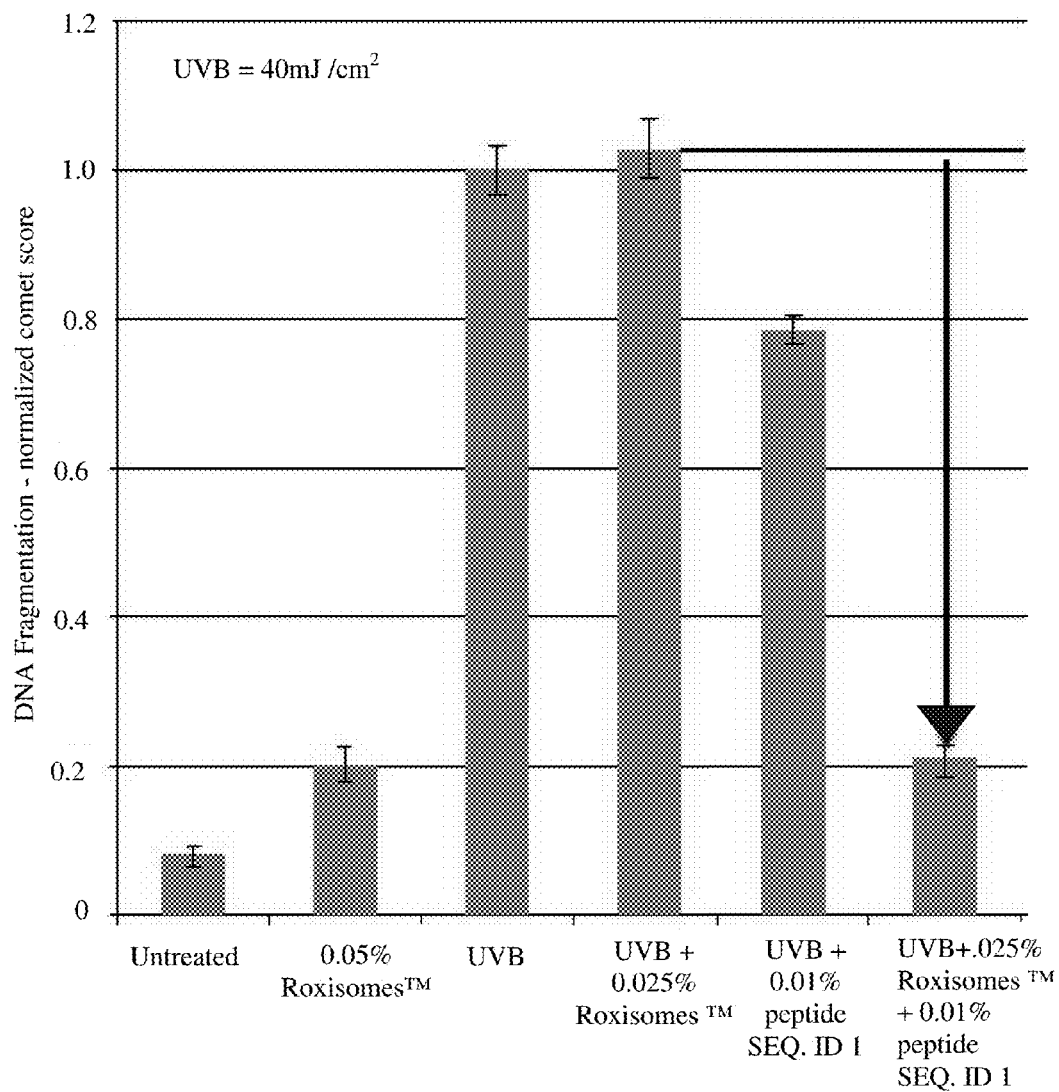
FIG. 2 shows the effects of an *Arabidopsis thaliana* extract containing 8-Oxoguanine glycosylase on DNA fragmentation in NHEK exposed to UVB radiation. The figure also shows the effects of a yeast ferment that contains the peptide SEQ ID No. 1.

We now show that treatment of normal human epidermal keratinocytes (NHEK) by SIRT6 activator peptide SEQ ID No. 1, in combination with a DNA repair enzyme (OGG1) significantly reduced DNA fragmentation caused by UVB radiation, and does so synergistically. A description of the treatment follows.
Sample Preparation This study used control samples and five types of test samples. For all control and test samples, NHEK were grown on Trevigen Flare™ slides, and covered with a thin layer of Phosphate Buffered Saline. Thereafter, test samples of types 2-5 were exposed to 40 mJ/cm$^2$ of UVB radiation. Control samples received no further treatment. Type 1 test samples, which were not exposed to UVB radiation, were treated by adding Roxisomes™ (an extract of *Arabidopsis thaliana* comprising 8-Oxoguanine glycosylase in a liposomal formulation comprising lecithin and water) to achieve a 0.05% solution in media. Type 2 samples received no further treatment. Type 3 test samples were further treated by adding Roxisomes™, to achieve a 0.025% solution in media. Type 4 samples were further treated by adding an hydrolyzed yeast extract that comprises about 2% peptide SEQ ID No. 1 (Ashland, Inc. Covington, Ky.), to achieve a 0.5% solution in media (equivalent to about 0.01% of the peptide in solution). Type 5 samples were further treated by adding Roxisomes™ (0.025%) and the yeast extract (0.5%) to the media. All samples were allowed to incubate for 4 hours prior to comet assay, which was performed as described above.
Results In FIG. 2, DNA fragmentation is normalized to test samples of type 2 (those irradiated with UVB, but receiving no pre-treatment). On that scale, the control samples had a normalized comet score of about 0.075, while the type 1 test samples (treated with Roxisomes™, but not irradiated) showed had a comet score of about 0.2, indicating that Roxisomes™ is speeding up DNA fragmentation. Type 3 samples (treated with the Roxisomes™ and then exposed to UVB radiation) had a comet score of about 1.025, again, indicating that Roxisomes™ is speeding up DNA fragmentation. Type 4 test samples (treated with the yeast extract and then exposed to UVB radiation) had a comet score of about 0.78, a 22% decrease compared to the type 2 test samples. This is consistent with the results of Example 1. Type 5 test samples (treated with Roxisomes™ and yeast extract and then exposed to UVB radiation) had a comet score of about 0.21, a 79% decrease compared to the type 2 test samples.

DISCUSSION

When used by itself, Roxisomes™ (8-Oxoguanine glycosylase (OGG1)) appears to increase DNA fragmentation in NHEK. When used by itself, a yeast ferment extract that comprises peptide SEQ ID No. 1 appears to stimulate SIRT6 to repair DNA fragmentation due to UVB exposure; a 22% improvement. When used in combination, the yeast ferment extract and Roxisomes™ appear to stimulate SIRT6 to repair DNA fragmentation due to UVB exposure; a whopping 79% improvement. This was wholly unexpected, especially since Roxisomes™ used by itself appears to increase DNA fragmentation in NHEK. We conclude that combinations of peptide SEQ ID No. 1 and OGG1 work synergistically to stimulate SIRT6 levels in NHEK, leading to a very high level of repair of DNA fragmentation caused by UVB radiation.

Compositions of the Invention

Suggested concentrations of SIRT6 activating peptide (SEQ. ID 1) range from 0.0001 to 1% by weight of the total composition, preferably from about 0.001 to about 0.1%, more preferably from about 0.005% to about 0.02%. In some preferred embodiments, the activating peptide may be supplied as a component of a yeast extract. In that case, the peptide content of the extract must be known in order to ensure that the composition comprises from 0.0001 to 1% of the peptide (SEQ. ID 1).

Suggested concentrations of 8-Oxoguanine glycosylase (OGG1) are from about 0.0001% to about 0.05%, preferably from about 0.0005% to about 0.01%, more preferably from about 0.001% to about 0.005%, with respect to the total weight of the final composition. Suggested concentrations of Roxisomes™ are about 0.02% to about 10%. preferably from about 0.1% to about 2%, more preferably from about 0.2% to about 1%, with respect to the total weight of the final composition.

The composition of the invention may be in the liquid, semi-solid, or solid form, and may be in the emulsion, solution, suspension, or anhydrous form. If in the solution or suspension form, the composition may contain from about 50 to 99.9% water. If in the emulsion form, the composition may contain from about 5-95% water and from about 5-95% oil. If in the anhydrous form, the composition may comprise from about 10-99% oil and 10-99% solidifying agents. In the case where the compositions are in the form of aqueous solutions, dispersions or emulsions, in addition to water the aqueous phase may contain one or more aqueous phase structuring agents, that is, an agent that increases the viscosity or, or thickens, the aqueous phase of the composition. This is particularly desirable when the composition is in the form of a serum or gel. Suitable ranges of aqueous phase structuring agents, if present, are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like.

In the event that a composition of the invention is in the emulsion form, then the composition will comprise an oil phase. Oily ingredients are desirable for the skin moisturizing and protective properties. Suitable oils include silicones, esters, vegetable oils, synthetic oils, including but not limited to those set forth herein. The oils may be volatile or non-volatile, and are preferably in the form of a pourable liquid at room temperature. The term "volatile" means that the oil has a measurable vapor pressure, or a vapor pressure of at least about 2 mm of mercury at 20° C. The term "non-volatile" means that the oil has a vapor pressure of less than about 2 mm of mercury at 20° C. Suitable volatile oils generally have a viscosity ranging from about 0.5 to 5 centistokes 25° C., and include linear silicones, cyclic silicones, paraffinic hydrocarbons, or mixtures thereof. Non-volatile oils generally have a viscosity of greater than about 5 to 10 centistokes at 25° C., and may range in viscosity up to about 1,000,000 centipoise at 25° C. Examples of non-volatile oils include, but are not limited to esters in the mono-, di-, or triester form.

In the case where the composition is anhydrous or in the form of an emulsion, it may be desirable to include one or more oil phase structuring agents in the cosmetic composition. The term "oil phase structuring agent" means an ingredient or combination of ingredients, soluble or dispersible in the oil phase, which will increase the viscosity, or structure, the oil phase. The structuring agent may be present in an amount sufficient to provide a liquid composition with increased viscosity, a semi-solid, or in some cases a solid composition that may be self-supporting. The structuring agent itself may be present in the liquid, semi-solid, or solid form. Suggested ranges of structuring agent are from about 0.01 to 70%, preferably from about 0.05 to 50%, more preferably from about 0.1-35% by weight of the total composition.

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

Optionally, but preferably, compositions of the invention will be formulated to have a certain SPF (sun protective factor) values ranging from about 1-100, preferably about 5-80, most preferably about 5-50%. Calculation of SPF values is well known in the art. To achieve this, it may be desirable to include in the composition one or more chemical UVA or UVB sunscreens or physical sunscreens in the particulate form.

The term "UVA sunscreen" means a chemical compound that blocks UV radiation in the wavelength range of about 320 to 400 nm. The composition may contain from about 0.001-20%, preferably 0.005-5%, more preferably about 0.005-3% by weight of the composition of UVA sunscreen. Examples of UVA sunscreen compounds include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane. Other types of UVA sunscreens include dicamphor sulfonic acid derivatives, such as terephthalylidene dicamphor sulfonic acid.

The term "UVB sunscreen" means a compound that blocks UV radiation in the wavelength range of from about 290 to 320 nm. Generally, the amount of the UVB chemical sunscreen present may range from about 0.001-45%, preferably 0.005-40%, more preferably about 0.01-35% by weight of the total composition. A variety of UVB chemical sunscreens exist including alpha-cyano-beta,beta-diphenyl acrylic acid esters such as 2-ethylhexyl 2-cyano-3,3-diphenylacrylate. Other suitable sunscreens include benzylidene camphor derivatives. Also suitable are cinnamate derivatives, such as ethylhexyl methoxycinnamate. Also suitable as UVB screening agents are various benzophenone derivatives including Benzophenone 1, 2, 3, 4, 5, 6, 7, 8, 9, 10, 11, and 12. Particularly preferred are Benzophenone 3, Benzophenone 4 and Benzophenone 5. Also suitable are certain menthyl salicylate derivatives, such as homomenthyl salicylate or menthyl anthranilate. Salicylate derivatives are also acceptable UVB absorbers.

The composition may contain 0.001-8%, preferably 0.01-6%, more preferably 0.05-5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, methyl paraben, propyl paraben, diazolidinyl urea, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM hydantoin, DEDM hydantoin dilaurate, dehydroacetic acid, diazolidinyl urea, dibromopropamidine diisethionate, DMDM hydantoin, and the like. In one preferred embodiment the composition may be free of parabens.

In general, any composition according to the invention may be prepared by separately combining oil phase ingredients and water phase ingredients, and mixing well. Any step required for forming an emulsion or otherwise imparting a structure to the finished composition will not interfere with the efficacy of the present invention.

Following several examples of skin care compositions according to the present invention, which are set forth for the purposes of illustration only.

Anti-Aging Cream (Examples 1, 2)

|  | 1 | 2 |
|---|---|---|
| water | Q.S. | Q.S. |
| caffeine | 0.01 | 0.02 |
| disodium EDTA | 0.01 | 0.05 |
| citric acid | 0.002 | 0.02 |
| butylene glycol | 3.20 | 5.44 |
| glycerine | 1.25 | 2.63 |
| tocopheryl acetate | 0.10 | 0.52 |
| ergothioneine | 0.00005 | 0.0005 |
| acetyl hexapeptide-8 | 0.0001 | 0.001 |
| *Roxisomes ™ | 0.10 | 0.40 |
| algae extract | 0.015 | 0.077 |
| *Cordyceps sinensis* | 0.01 | 0.02 |
| *Boswellia serrata* extract | 0.01 | 0.02 |
| *laminaria digitata* extract | 0.007 | 0.015 |
| *Narcissus tazetta* bulb extract | 0.002 | 0.004 |
| *cucumis sativis* (cucumber) fruit extract | 0.00006 | 0.015 |
| hyaluronic acid | 0.01 | 0.05 |
| dimethicone | 2.50 | 21.17 |
| peptide SEQ. ID 1 | 0.02 | 0.04 |
| phenoxyethanol | 0.36 | 0.54 |
| fragrance | 0.25 | 0.40 |

*Roxisomes ™: water/yeast fermentation extract of *Arabidopsis thaliana*/lecithin comprising 0.5% 8-Oxoguanine glycosylase (OGG1).

Skin Mist (Example 3)

| PART A | |
|---|---|
| water | 91.07 |
| polyquaternium-4 | 0.05 |
| citric acid | 0.01 |
| propylene glycol | 2.00 |
| methylparaben | 0.20 |
| Roxisomes ™ | 0.05 |
| PART B | |
| sodium PCA | 2.00 |
| hydrolyzed collagen | 2.00 |
| panthenol | 0.10 |
| *aloe vera* gel | 1.00 |
| dimethicone copolyol | 0.30 |
| diazolidinyl urea | 0.20 |
| PART C | |
| TEA-cocoyl glutamate | 0.50 |
| polysorbate 20 | 0.50 |
| peptide SEQ. ID 1 | 0.01 |
| fragrance | 0.01 |

In main kettle, heat water to 70° C. Disperse polyquaternium-4 with agitation. Add remaining Part A ingredients except Roxisomes™. Cool to 50° C. Add Roxisomes™. Add Part B ingredients one a time, with mixing. Cool to 40° C. Add premixed Part C to main kettle.

Oil in Water Skin Cream (Example 4)

| PART A | |
|---|---|
| A-C copolymer 540 | 2.00 |
| mineral oil | 5.00 |
| Dow fluid 556 | 1.00 |
| Emerest 2388 | 10.5 |
| Amerchol 400 | 2.0 |
| Solulan 25 | 1.0 |
| Arlacel 60 | 2.0 |
| PART B | |
| sorbitol (70%) | 5.0 |
| Tween 60 | 1.0 |
| Carbopol 940 | 0.75 |
| Germall 115 | 0.4 |
| triethanolamine | 0.75 |
| water | 68.38 |
| PART C | |
| Roxisomes ™ | 0.1 |
| peptide SEQ. ID 1 | 0.02 |
| fragrance | 0.1 |

Slowly mix Part A and heat to 85° C. Mix Part B. Disperse Carbopol in water; add remainder of Part B, except TEA; heat to 85° C. Add Part B to Part A with shearing. Add TEA with shearing while cooling to 40° C. Add Part C below 40° C.

Oil in Water Skin Lotion (Example 5)

| Part A | |
|---|---|
| wax | 3.6 |
| mineral wax | 2.1 |
| Amerchol L-101 | 5.2 |

| | |
|---|---|
| jojoba oil | 2.1 |
| glycerol monostearate | 2.1 |
| Part B | |
| triethanolamine | 1.0 |
| propylene glycol | 4.7 |
| water | 69.3 |
| preservatives | 1.0 |
| Part C | |
| fragrance | 0.1 |
| Roxisomes ™ | 8.0 |
| peptide SEQ. ID 1 | 0.8 |

Mix Part A and heat to 80° C. Mix Part B and hat to 80° C. Add Part B to Part A with agitation. Cooling to 40° C. Add Part C below 40° C.

Sunscreen (Example 6)

| | |
|---|---|
| 4-tert-Butyl-4-methoxydi-benzoylmethane | 2.0 |
| amyl N,N-dimethyl-p-aminobenzoate | 3.0 |
| 2-hydroxy-4-methoxybenzophenone | 2.0 |
| cetyl alcohol | 3.0 |
| stearic acid | 3.0 |
| petrolatum | 3.0 |
| olive oil | 3.0 |
| squalene | 5.0 |
| propylene glycol | 3.0 |
| Roxisomes ™ | 10.0 |
| potassium hydroxide | 0.2 |
| talc | 5.0 |
| trisodium EDTA | 0.02 |
| peptide SEQ. ID 1 | 1.0 |
| water | q.s. to 100% |

Wound Healing Accelerator (Example 7)

| | |
|---|---|
| polyoxyethyleneglycol monostearate | 2.0 |
| glyceryl monostearate | 5.0 |
| stearic acid | 5.0 |
| behenyl alcohol | 1.0 |
| mineral oil | 1.0 |
| glyceryl trioctanoate | 5.0 |
| kojic acid dipalmitate | 2.0 |
| 1,3 butylene glycol | 5.0 |
| allantoin | 0.1 |
| Roxisomes ™ | 0.2 |
| peptide SEQ. ID 1 | 0.01 |
| water | q.s. to 100% |

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

What is claimed is:

1. A method for repairing DNA fragmentation due to UVB exposure in skin cells in need of such treatment, the method comprising the step of topically applying a composition that comprises 0.0001% to 1% of a SIRT6 activating peptide and 0.0001%-0.05% of 8-Oxoguanine glycosylase, by weight of the composition, wherein the SIRT 6 activating peptide is (SEQ ID No. 1)

G-A-G-V-S-A-E-NH$_2$
Gly-Ala-Gly-Val-Ser-Ala-Glu-NH$_2$.

2. A composition that comprises 0.0001% to 1% of a SIRT6 activating peptide and 0.0001%-0.05% of 8-Oxoguanine glycosylase, by weight of the composition, wherein the SIRT 6 activating peptide is (SEQ ID No. 1)

G-A-G-V-S-A-E-NH$_2$
Gly-Ala-Gly-Val-Ser-Ala-Glu-NH$_2$.

* * * * *